(12) United States Patent
Van de Casteele

(10) Patent No.: US 6,861,066 B2
(45) Date of Patent: Mar. 1, 2005

(54) METHOD FOR THE DELIVERY OF A BIOLOGICALLY ACTIVE AGENT

(75) Inventor: Russell Van de Casteele, Deerfield Beach, FL (US)

(73) Assignee: Health Plus International Inc., Deerfield Beach, FL (US)

(*) Notice: Subject to any disclaimer, the term of this patent is extended or adjusted under 35 U.S.C. 154(b) by 79 days.

(21) Appl. No.: 10/096,337

(22) Filed: Mar. 11, 2002

(65) Prior Publication Data

US 2003/0170311 A1 Sep. 11, 2003

(51) Int. Cl.⁷ .............................. A61K 9/10; A61K 9/02; A61K 9/12
(52) U.S. Cl. ...................... 424/435; 424/434; 424/436; 424/451; 424/474; 424/45; 514/944
(58) Field of Search ................................. 424/434, 435, 424/436, 451, 474, 45, 489

(56) References Cited

U.S. PATENT DOCUMENTS

| | | |
|---|---|---|
| 4,946,870 A | 8/1990 | Partain, III et al. |
| 5,056,511 A | 10/1991 | Ronge |
| 5,271,944 A | 12/1993 | Lee |
| 5,681,600 A | 10/1997 | Antinone et al. |
| 5,858,410 A | 1/1999 | Muller et al. |
| 5,891,465 A | 4/1999 | Keller et al. |
| 5,981,591 A | 11/1999 | Deihl |
| 2003/0072801 A1 * | 4/2003 | Curatolo et al. ............ 424/465 |

OTHER PUBLICATIONS

International Journal of Pharmaceutics, Gandhi et al.; "Mechanisms of penetration enhancement for transbuccal delivery of salicylic acid", vol. 85, (1992), pp. 129–140.*

International Journal of Pharmaceutics, Aungst et al.; "Comparison of the effects of various transmucosal absorption promoters on buccal insulin delivery", vol. 53, 3, (1989), pp. 227–235.

Journal of Pharmaceutical Sciences, Ch'ng et al.; "Bioadhesive Polymers as Platforms for Oral Controlled Drug Delivery II", vol. 74, 4, (1985), pp. 399–405.

* cited by examiner

Primary Examiner—Thurman K. Page
Assistant Examiner—J. Venkat
(74) Attorney, Agent, or Firm—McHale & Slavin

(57) ABSTRACT

A method of manufacturing a stable nanosuspension for delivery of a biologically active agent into the bloodstream of a subject is disclosed. A microfluidizable mixture is initially formed and processed via a microfluidization process to form the stable nanosuspension, which may be administered via the buccal mucosa or other suitable routes of administration. This product demonstrates increased bioavailability, enhanced period of onset, and enhanced stability for a controlled-release product.

8 Claims, 1 Drawing Sheet

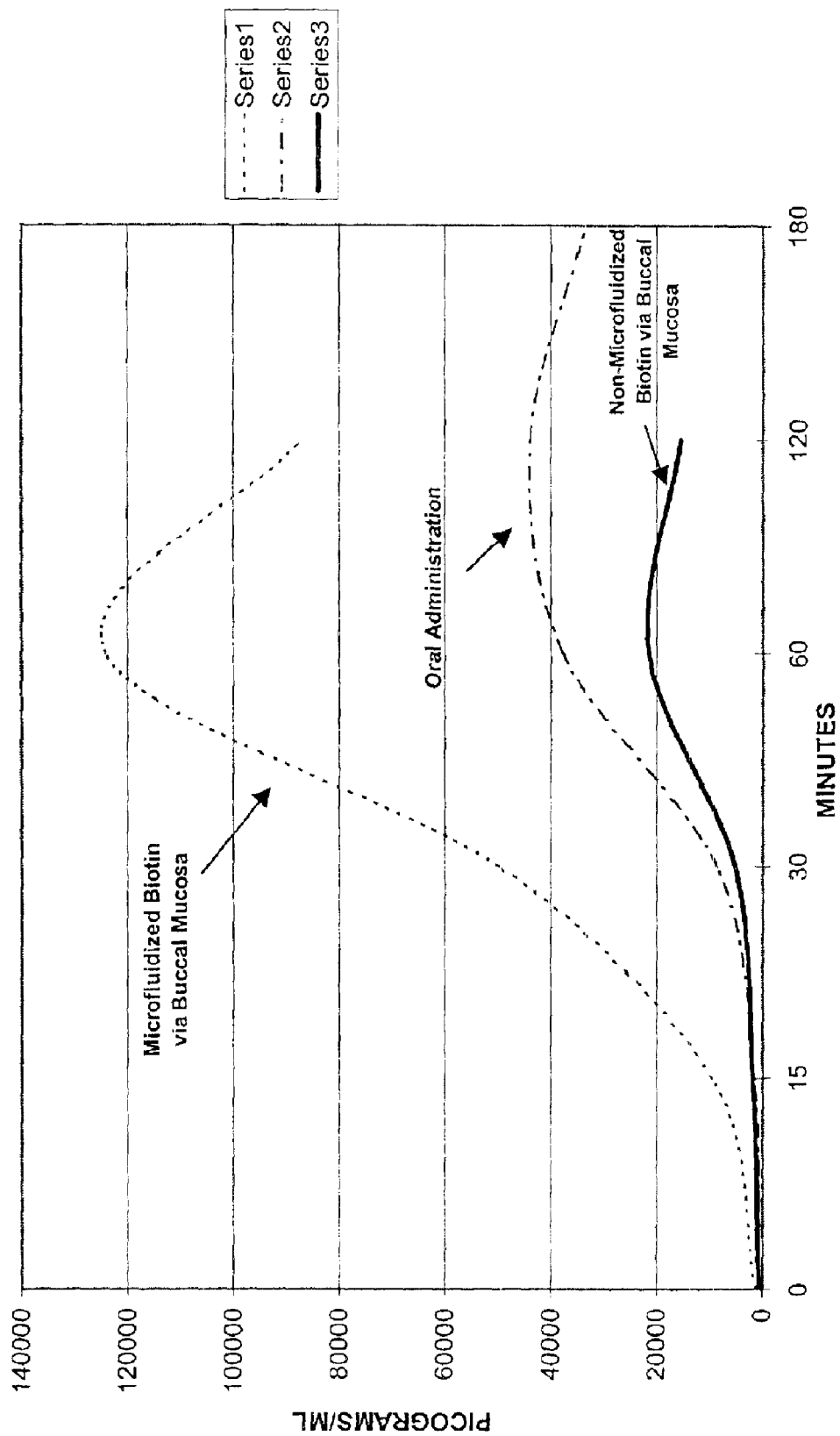

METHOD FOR THE DELIVERY OF A BIOLOGICALLY ACTIVE AGENT

FIELD OF THE INVENTION

The present invention relates to the administration of biologically active agents and more particularly to a method for enhancing absorption and stability of an agent into the bloodstream by forming, via a microfluidization technique, a stable uniform submicron emulsion or nanosuspension, for delivery of biologically active agents via multiple pathways, particularly via the buccal mucosa.

BACKGROUND OF THE INVENTION

Biologically active agents such as nutritional supplements, hormones, and a variety of pharmaceutical preparations, which will generally be referred to as "drugs' are typically provided in oral (liquids or solids) or injectable dosage formulations, however there are many disadvantages associated with this type of administration.

Many of the ingredients are degraded within the gastrointestinal (GI) tract or undergo first-pass metabolism in the liver. In addition, there exists a segment of the population who experience difficulty swallowing pills or are unable to tolerate any solids.

During the past three decades, however, formulations that control the rate and period of drug delivery (e.g., time-release medications) and target specific areas of the body for treatment have become increasingly common and complex. Some have provided solutions to the problem of administering different types of drugs but there are still a large number of medications that do not achieve maximum pharmaceutical effect because they do not reach the intended tissue targets either fast enough or in high enough concentrations.

The potency and therapeutic effects of many drugs are limited or reduced because of the partial degradation that occurs before they reach a desired target in the body. Further, injectable medications could be made less expensively and administered more easily if they could simply be dosed by other routes such as the oral mucosa, the pulmonary mucosa or through the vaginal and intestinal tract. However, this improvement cannot happen until methods are developed to safely shepherd drugs through these specific areas of the body, where different physiological environments (e.g. low pH values in the stomach) can destroy a medication or where absorption is not rapid or complete, or through an area where healthy tissue might be adversely affected.

Transmucosal routes of drug delivery offer distinct advantages. Of the various routes, the mucosal linings of the nasal passages and the oral cavity are the most attractive. Although the nasal route has reached commercial success with several drugs, such as with allergy medications, potentially serious side-effects, such as irritation and possibly irreversible damage to the ciliary action of the nasal cavity from chronic application, have deterred health professionals from recommending their long-term use.

Within the oral cavity, there are three generally recognized routes of administration of a biologically active agent. Local delivery is mainly limited to applications regarding disruptions occurring within the oral cavity itself, such as a canker sore. Sublingual delivery is achieved through the mucosal membranes lining the floor of the mouth. This route provides rapid absorption and has reached commercial status with biologically active agents such as nitroglycerin, which is placed under the tongue. Because of the high permeability and the rich blood supply, transport via the sublingual route results in a rapid onset of action, providing a delivery route appropriate for highly permeable drugs with short delivery period requirements and an infrequent dosing regimen. The negative however, is that it produces a saliva wash (swallowing) and in the case of nitrolinqual it has been found to cause headaches as a result of administering excess of the drug needed to accomplish it's task.

The third generally recognized route is the buccal mucosa. This area encompasses the mucosal membranes of the inner lining of the cheeks. This area also has a rich blood supply, is robust, and provides a short cellular recovery time following stress or damage. Although the buccal mucosa is less permeable than the sublingual area, the expanse of smooth and relatively immobile mucosa provide a highly desirably absorption pathway for sustained-release and controlled-release delivery of biologically active agents. As with other transmucosal routes of administration, two major advantages include avoiding hepatic first-pass metabolism and pre-systemic elimination within the GI tract.

One of the major disadvantages associated with buccal mucosa delivery of a biologically active agent has been the relatively low passage of active agents across the mucosal epithelium, thereby resulting in low agent bioavailability, which translates into a substantial loss usable active agent within each dosage. Various permeation and absorption enhancers such as POLYSORBATE-80, Sorbitol, and phosphatidylcholine have been explored to improve buccal penetration. Studies have indicated that the superficial layers and protein domain of the epithelium may be responsible for maintaining the barrier function of the buccal mucosa (Gandhi and Robinson, Int. J. Pharm. (1992) 85, pp129–140).

Additionally, it is known that use of a permeation enhancer can increase the passage of a biomolecule. Furthermore, studies have suggested the feasibility of buccal delivery of even a rather large molecular weight pharmaceutical (Aungst and Rogers, Int. J. Pharm. (1989) 53, pp227–235).

A further area of investigation includes the use of bioadhesive polymers in buccal delivery systems. Bioadhesive polymers have been developed to adhere to a biological substrate in order to maintain continual contact of an agent with the site of delivery. This process has been termed mucoadhesion when the substrate is mucosal tissue (Ch'ng et al., J. Pharm. Sci. (1985) 74, 4, pp399–405).

The goal of all drug delivery systems is to deploy medications intact to specifically targeted parts of the body through a medium that can control the therapy's administration by means of either a physiological or chemical trigger.

To achieve this goal, a number of researchers have turned to advances in micro and nanotechnology. One prominent area of endeavor is the production of so-called "nanoparticles" which act as chemical or physical "carriers" of drugs.

During the past decade, novel polymeric microspheres, polymer micelles, and hydrogel-type materials have been shown to be effective in enhancing drug targeting specificity, lowering systemic drug toxicity, improving treatment absorption rates, and providing protection for pharmaceuticals against biochemical degradation. These are all goals of drug delivery. In addition, several other experimental drug delivery systems show signs of promise, including those composed of biodegradable polymers, dendrimers (so-called star polymers), electroactive polymers, and modified C-60 fullerenes (also known as "buckyballs.")

Polymer drug delivery systems are based on "carriers" which are composed of mixing polymeric chemical compounds with drugs to form complex, large molecules, which "carry" the drug across physiological barriers.

Illustrative examples of these polymeric compounds are poly(ethylene-glycol)-poly(alpha, beta-aspartic acid), carboxylates, and heterobifunctional polyethylene glycol, in addition to others.

Another type of nanotechnology revolves around the use of "hydrogels" as carriers of drugs. The principle behind this technology is to use a chemical compound which traps a drug and then releases the active compound by "swelling" or expanding inside of specific tissues, thus allowing a higher concentration of the drug in a biodegradable format. Hydrogels are very specialized systems and are generally formulated to meet specific needs for the delivery of individual drugs.

During the past two decades, research into hydrogel delivery systems has focused primarily on systems containing polyacrylic acid (PAA) backbones. PAA hydrogels are known for their super-absorbency and ability to form extended polymer networks through hydrogen bonding. In addition, they are excellent bioadhesives, which means that they can adhere to mucosal linings within the gastrointestinal tract for extended periods, releasing their encapsulated medications slowly over time.

One example of the complexity of these systems is a glucose-sensitive hydrogel that could be used to deliver insulin to diabetic patients using an internal pH trigger. This system features an insulin-containing "reservoir" formed by a poly[methacrylic acid-g-poly(ethylene glycol)]hydrogel membrane into which glucose oxidase has been immobilized. The membrane itself is housed between nonswelling, porous "molecular fences".

Although these approaches are the focus of intense research, other processes are also under consideration, including aerosol inhalation devices, transdermal methodologies, forced-pressure injectables, and biodegradable polymer networks designed specifically to transport new gene therapies.

Another method to formulate drugs for delivery has been the use of nanosuspensions of drugs for reducing size and creating uniform suspensions. The use of commercial devices such as mill processors, microfluidizers and homogenizers has allowed the formulation of nanosuspensions of various substances. Nanosuspended drugs can also be wrapped in liposomes or made into micellar mixtures by mixing the drug preparations with appropriate chemical compounds.

Prior artisans have explored a variety of avenues in an effort to produce a viable and efficient means for buccal mucosal delivery. Such avenues include the use of liposomal carriers to enhance uptake or facilitate the delivery of a product; decreasing the particle size of microspherical carriers, or employing a physical matrix, such as a sponge, to hold a medicinal product at the buccal area.

What is lacking in the art is a method for increasing the bioavailability of a biologically active agent, which may be administered via various routes, but particularly with regard to administration via the buccal mucosa; and a stable product useful for carrying out the method.

DESCRIPTION OF THE PRIOR ART

U.S. Pat. No. 5,681,600 discloses a stable, liquid nutritional product and a method for its manufacture. Preparation of the product comprises forming a protein solution, a carbohydrate solution, and an oil blend to combine with an amount of a nutritional ingredient containing soy polysaccharide. Soy polysaccharide is essential as a stabilizer to maintain the components in solution, thereby avoiding the need for carrageenan, and to reduce the need to overfortify the amount of nutritional ingredient included, owing to inherent degradation over time. The combined solution is subjected to microfluidization as an alternative to homogenization. The reference fails to suggest forming a stable uniform submicron emulsion as a means for increasing bioavailability and stability of the final product.

U.S. Pat. No. 5,056,511 discloses a method for compressing, atomizing, and spraying liquid substances for inhalation purposes. The liquid substance is compressed under high pressure to reduce its volume. The released liquid is then atomized to cause the liquid substance to burst into particles in the size range of about $0.5\mu$ to about $10\mu$, thereby forming a very fine cloud for direct inhalation buy the end-user. This method is intended for immediate use, and does not provide a product having the stability of the product disclosed herein. The reference also fails to suggest forming a stable uniform submicron emulsion as a means for increasing bioavailability and stability of the final product.

U.S. Pat. No. 4,946,870 discloses a film-forming delivery system, which requires at least one aminopolysaccharide, useful for delivery of pharmaceutical or therapeutic active agents to a desired topical or mucous membrane site. The delivery of active agent may be in the form of a gel, patch, sponge, or the like.

U.S. Pat. No. 5,891,465 discloses the delivery of a biologically active agent in a liposomal formulation for administration into the mouth. The phospholipid vesicles of the liposomal composition provide an increase in bioavailability of the biologically active agent in comparison to an oral dosage form. The liposomal composition, while reaching a submicron level for absorption into the bloodstream, nevertheless requires specific components to be provided within a narrow range of concentration in order to enable the one or more bilayer forming lipids to achieve delivery through the mucosal lining.

U.S. Pat. No. 5,981,591 discloses a sprayable analgesic composition and method of use. The sprayable dosage includes one or more surfactants for facilitating the absorption through the surface of the buccal mucosa of the mouth. The use of surfactants for increasing bioavailability is of limited value, since they are only effective for a small proportion of biologically active agents. The reference fails to provide a stable uniform submicron emulsion, thus failing to achieve the enhancements in absorption time, bioavailability, stability, and controlled-release demonstrated by the instant invention.

Drug preparations called nanosuspensions were produced by high-pressure homogenization, and are the subject of U.S. Pat. No. 5,858,410 to Muller.

Prior to the use of high pressure homogenization, nanosuspensions were prepared by a pearl milling process, which was a longer process than pressure homogenization. This technology is the subject of U.S. Pat. No. 5,271,944 to Lee. A number of other methods have been used to prepare nanosuspensions with various degrees of success including low energy agitators, turbine agitators, colloid mills, sonolators, orifices, media mills, rotor stator mixers and sonicators.

There is no suggestion in the prior art regarding the production of nanosuspensions via a microfluidization technique nor for the use of said nanosuspensions for the delivery of biologically active agents, e.g. vitamins; and conspicuously lacking is any suggestion of administration of said biologically active agent containing nanosuspensions via a buccal mucosal route.

SUMMARY OF THE INVENTION

The present invention is directed toward a method for creating microfluidized preparations, which define stable uniform submicron emulsions, or nanosuspensions, which enable enhanced delivery of a biologically active agent into the bloodstream of a subject.

The microfluidized preparations of the instant invention can be prepared as aqueous or organic solutions or as emulsions, using known emulsifying agents, and can be delivered by way of a microfluidized spray, an aerosol, a tablet, a pill, a liquid, a suppository, or a gel. Delivery may be accomplished by parenteral, intrathecal, intravenous, transdermal, transmucosal, and any or all commonly recognized methods for drug delivery.

The instant inventor has utilized a microfluidization technique for the production of microsuspensions of aqueous and oil-based solutions for use in drug delivery systems. The instant process does not require encapsulation in polymers or the use of hydrogels or other supporting or encapsulating substances. Chemicals prepared in this manner are called "nanosuspensions." This process allows molecules to be embedded into microdroplets of between about 87 nm to about 10 $\mu$m in size, which are used to create stable and uniform emulsions and dispersions.

The nanosuspensions of the instant invention are effective in providing higher concentrations of a molecule in the bloodstream over a longer period of time as compared to molecules prepared by other pharmacological methods and similarly delivered, e.g. by a buccal mucosal route, intestinal absorption, or the like. While not wishing to be bound to any particular theory of operation, it has been hypothesized that the nanosuspensions of the instant invention allow molecules to be delivered across tissue barriers at a more even rate than non-microfluidized preparations.

In its broadest context, the method includes mixing together various aqueous and/or non-aqueous components, e.g. organic or inorganic components, and forming at least one solution. Depending upon the solubility of the biologically active agent, a microfluidizable mixture may be obtained by adding the agent to either an aqueous solution, an organic solution, or a crude emulsion which is a mixture of said organic and inorganic solutions. The microfluidizable mixture may further contain various components such as flavorings, preservatives, surfactants, and permeation enhancers known in the art. Microfluidizing said mixture provides a means for the mixture to form a stable uniform submicron emulsion. It is this emulsion which provides for the enhanced period of onset, bioavailability, and controlled-release capability of the final product. Upon contact of the emulsion with the body, e.g. with an area of the oral cavity including the buccal mucosa, the agent is absorbed into the bloodstream in an amount sufficient to elicit a desired biological response.

Accordingly, it is an objective of the instant invention to provide a biologically active agent as a stable uniform nanosuspension, produced via a microfluidization process, and effective for administration via various routes, and particularly the buccal mucosa.

It is a further objective of the instant invention to provide a biologically active agent capable of an efficient period of onset.

It is yet another objective of the instant invention to provide a biologically active agent capable of submicron stability.

It is a still further objective of the invention to provide a biologically active agent capable of increased bioavailability through various routes, particularly the buccal mucosal route.

It is a further objective of the instant invention to provide a biologically active agent capable of sustained-release or controlled-release action.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objectives and features thereof.

BRIEF DESCRIPTION OF THE FIGURES

FIG. 1 is a graphic comparison of mucosal absorption of microfluidized biotin and non-microfluidized biotin versus oral administration of commercially available biotin for absorption via the gastro-intestinal tract.

DETAILED DESCRIPTION OF THE INVENTION

This application is directed towards a novel application of nanosuspensions for delivery of biological agents, either singly or in various combinations, e.g. multi-vitamin/mineral supplements. As an illustrative, albeit non-limiting example, we have demonstrated that a common vitamin, biotin, when administered as a buccal spray achieves higher blood levels as a nanosuspension when compared to the same vitamin administered after preparation in normal solution without microfluidization and administered in the same fashion. By extension, this application applies to all biologically active agents.

While not wishing to be bound to any particular theory of operation, there are several hypothetical mechanisms that may account for the increased absorption of biotin, or alternative biologically active agents, when formulated as a nanosuspension and administered via the buccal mucosal route.

1. There is a greater concentration of drug at the active mucosal surface (there are two possible explanations for this phenomenon):

a. Increased Saturation at the Mucosal Membrane

The reduced size of the microdroplets in the nanosuspension (which concentrates more molecules in a smaller unit volume of fluid) allows a greater number of molecules to come into contact with the mucosal membrane, over a shorter period of time. This increases the adhesiveness of the drug to the surface of the buccal membrane and enhances the probability that more molecules will be absorbed than from non-microfluidized preparations;

b. Increased Passive Infusion

As a result of the increased local concentration of drug, there may be greater passive diffusion gradient across the mucosal membrane, ultimately resulting in greater plasma levels.

2. Nanosuspensions stimulate active transport of the molecules across the mucosal membrane:

In adopting this explanation, it is theorized that the nanodroplets could stimulate greater "active transport" of compounds across the mucosal membrane by bringing a greater concentration of biotin into contact with specific receptor sites.

The present invention provides a method for the delivery of a biologically active agent enhanced by the formation of a stable uniform submicron emulsion, termed a nanosuspension. While illustrative examples are limited to human subjects, the technology is in no way limited by said examples. The nanosuspensions which are the subject of the instant invention are contemplated for use in either a medical or veterinary setting, and may be administered in any reasonable fashion as is known in the art. The preferred embodiment, as thoroughly illustrated herein, is preferably formulated to be sprayed into the mouth of a human subject or an animal, whereby absorption via the buccal mucosa is accomplished.

A "biologically active agent", "biological agent", or "agent", as used herein, refers to any synthetic or natural element or compound, protein, cell, or tissue including a pharmaceutical, drug, therapeutic, nutritional supplement, herb, hormone, or the like, or any combinations thereof, which when introduced into the body causes a desired biological response, such as altering body function or altering cosmetic appearance.

To convert the microfluidizable mixture to the stable uniform submicron emulsion of the present invention, the mixture is subjected to an ultra-high energy mixing device. This is preferably achieved through the process of microfluidization.

The MicroFluidizer Processor is a device that provides high shear rates, maximizing the energy-per-unit fluid volume to produce uniform submicron particle and droplet sizes of chemical or particulate substances.

Process pressures are highly variable, ranging from a low of 1,500 to 23,000 psi, enabling the processing of a wide variety of fluids ranging from simple oil-in-water emulsions to high-weight-percent solids-in-liquid suspensions.

The MicroFluidizer contains an air-powered intensifier pump designed to supply the desired pressure at a constant rate to the product stream. As the pump travels through its pressure stroke, it drives the product at a constant pressure through precisely defined fixed-geometry microchannels within the interaction chamber. As a result, the product stream accelerates to high velocities, creating shear rates within the product stream that are orders of magnitude greater than any other conventional means. All of the product experiences identical processing conditions, producing the desired results, including: uniform particle and droplet size reduction (often submicron).

As a result of the high shear rate there is produced a mixture containing uniform submicron particles and the creation of stable emulsions and dispersions is achieved. This processing overcomes limitations of conventional processing technologies by utilizing high pressure streams that collide at ultra-high velocities in precisely defined microchannels. The final product is a stable uniform submicron emulsion, a "nanosuspension" composed of nanodroplets.

The stability and rate of absorption may be further enhanced by one or more components within the initial emulsion. In addition, the rate of absorption of the final product may be enhanced by the uniformity or size of the particles.

Permeation enhancers utilized in the present invention include the conventional physiologically acceptable compounds generally recognized as safe (GRAS) for human consumption. Any surfactant which assists in decreasing particle size is contemplated by the instant invention.

In order to examine the increased efficiency of absorption this formulation provides, initial experimentation was performed. A microfluidizable mixture including biotin as an agent was prepared.

Biotin is a water-soluble, B-complex vitamin that is necessary for the synthesis of fatty acids and nucleic acids. If biotin is absent in the body, the production of fat is impaired. The synthesis of niacin is dependent upon biotin.

Biotin has a rather unique structure with three asymmetric carbons and therefore eight different isomers are possible. Only one isomer has vitamin activity, d-biotin. It exists in natural foodstuffs in both bound and free forms and is also taken as a supplement.

Biotin is absorbed as the intact molecule in the first half of the small intestine. It is transported as a free water-soluble component of plasma, is taken up by cells via active transport, and is attached to its apoenzymes. All animal cells contain some biotin, with larger quantities in liver and kidneys.

Metabolically, biotin is an essential coenzyme in carbohydrate, fat, and protein metabolism is important in the conversion of carbohydrate to protein and vice versa, functions as maintaining normal blood glucose levels when carbohydrate intake is low, transports carboxyl units and fixes carbon dioxide (as bicarbonate) in tissue.

Bacteria synthesize biotin in the intestinal tract. A small amount of this water soluble vitamin is absorbed: however, the quantity that is not used is excreted through the urine. Raw eggs contain a compound called Avidin. Avidin has the same chemical structure as biotin. Because of this structural similarity, Avidin binds to biotin's receptor sites; therefore, biotin is unable to bind and is unable to be used.

The skin and hair mainly affected by a biotin deficiency causing baldness, dermatitis, and rashes around the mouth and nose. The locations that are commonly deficient in biotin are the male genitalia, bone marrow, liver, and the kidneys. Other symptoms of the deficiency are sleeplessness, poor appetite, and dry skin.

The following preparation procedure was followed:

An aqueous solution comprising purified water (64%) and glycerin (30%), acting as a solvent and taste enhancer, was stirred and heated to a temperature of about 60° C. Once complete dissolution was reached, the mixture was cooled to about 50° C. Biotin, (about 2%) potassium hydroxide (about 0.75%) and citric acid (as an acidulent/buffering agent) (about 0.1%) were added and the mixture was adjusted to a pH of about 8–9. The mixture was further cooled to about 40° C. and while stirring, POLYSORBATE-80 (about 0.5%) was added, which acted as an emulsifier and surface activator. Natural cranberry flavor (about 2.39%) and potassium sorbate (about 0.26%), a preservative, were then added. Upon reaching complete dissolution, the compound mixture appeared homogeneous, brown, and slightly transparent.

The crude emulsion was then passed through a model M-110Y MICROFLUIDIZER (Microfluidics Corporation, Newton, Mass.) under 18,000 psi. After a single pass, the mean particle size, according to a Horiba LA-910 particle size analyzer, was 151 nm.

The resulting stable uniform submicron emulsion was then placed into a spray vial with a fine mist nozzle. The particular nozzle provided thorough coverage of the oral cavity.

EXAMPLE 1

Absorption of Microprocessed Biotin and Non-processed Biotin via the Buccal Mucosa versus Oral Administration in a Normal Human Subject Objective: To compare the absorption rate and the total amount of absorption across the buccal mucosa of biotin prepared in microdroplets with the absorption rate and total absorption of a megadose of biotin contained in regular solution, in a normal healthy subject, when given by a spray applicator.

Utilizing a process, as outlined above, for producing microdroplets of aqueous and oil based solutions for use in drug delivery systems, formulations for testing were produced. The process allows molecules to be embedded into microdroplets of between about 87 nm and 10 μm in size, which are used to create stable and uniform emulsions and dispersions.

Theoretically, such dispersions should allow molecules to be delivered across tissue barriers at a more even rate than non-microfluidized or "normal" solutions. This should allow the accumulation of higher concentrations of a molecule in the blood stream over a longer period of time than with molecules prepared by standard pharmacological methods and delivered either by buccal mucosal or intestinal absorption.

By using the "microfluidization" process to prepare mixtures of biologically active agents, e.g. vitamins and other nutritional supplements, products may be designed, manufactured and standardized for use in spray applicators which deliver single dose sprays to the buccal mucosa. The purpose of this type of delivery is to introduce such biologically active agents, e.g. vitamins and minerals, into the body in a manner which allows, over time, more rapid, uniform and complete absorption than that which has been heretofore achieved via administration of non-microfluidized components in the form of pills, tablets, capsules or liquids which are absorbed through the gastrointestinal tract. In addition, the microfluidization process appears to offer increases in shelf-life, with testing showing a shelf-life of about 3 years.

In its physiologically active form biotin is attached at the active site of four important enzymes, known as carboxylases. Each carboxylase catalyzes an essential metabolic reaction.

Acetyl-CoA carboxylase catalyzes the binding of bicarbonate to acetyl-CoA to form malonyl-CoA. Malonyl-CoA is required for the synthesis of fatty acids.

Pyruvate carboxylase is a critical enzyme in gluconeogenesis, the formation of glucose from sources other than carbohydrates, for example, amino acids and fats.

Methylcrotonyl-CoA carboxylase catalyzes an essential step in the metabolism of leucine, an indispensable (essential) amino acid. Propionyl-CoA carboxylase catalyzes essential steps in the metabolism of amino acids, cholesterol, and odd chain fatty acids (fatty acids with an odd number of carbon molecules).

Histones are proteins that bind to DNA and package it into compact structures to form chromosomes. The compact packaging of DNA must be relaxed somewhat for DNA replication and transcription to occur. Modification of histones through the attachment of acetyl or methyl groups (acetylation or methylation) has been shown to affect the structure of histones, thereby affecting replication and transcription of DNA. The attachment of biotin to another molecule, such as a protein, is known as "biotinylation". The enzyme biotinidase has recently been shown to catalyze the biotinylation of histones, suggesting that biotin may play a role in DNA replication and transcription.

Methods

A normal human subject who had not taken supplements containing biotin for at least 48 hours before testing used a spray applicator to administer a single megadose of biotin (15 mg) by carefully spraying the inside of each cheek (buccal mucosa). A prebleed of 5 ml of blood, taken by routine venipuncture from an antecubital vein, was obtained before the biotin was administered and serial blood draws were obtained at 5, 10, 15, 30, 60 and 120 minutes after administration. Preparations of microprocessed biotin, non-processed biotin, and commercially available non-processed biotin in pill form were administered at different times in the same individual, subsequent to a period of time to enable washout, e.g. 1 week, thereby allowing an intrasubject comparison. The pill form of biotin was administered (18.75 pills at 800 mcg. each-increasing the surface area for better absorption) by swallowing, as instructed, and allowing absorption via the gastro-intestinal tract. Furthermore, blood was drawn at 180 minutes (an additional hour past that which was utilized for comparison of the microfluidized and non-microfluidized formulations) thereby yielding an additional datapoint.

Biotin was assayed from the whole blood in a commercial laboratory using a sensitive biological assay. In this assay, the flagellate *Ochromonas danica,* which has a sensitive biotin requirement for growth in culture, was mixed with dilutions of the subjects whole blood, incubated for 3–5 days and assayed for growth. Biotin was measured in picograms/ml. This test being more accurate than the common chemical HPLC assay.

Results

Data was recorded showing both the rate and amount of biotin adsorption in subject RV after administration of microprocessed biotin or non-processed biotin via the buccal mucosa and in pill form via the gastro-intestinal tract. Normal blood levels of biotin in individuals who have not taken supplements or who have not recently eaten foods high in biotin concentration within 24–48 hours are between 200–500 picograms/ml. FIG. 1 represents a graphic analysis of the data.

Based on this anecdotal trial in a human subject, microprocessed biotin, when given in megadose amounts, was absorbed in significantly higher amounts than non-processed biotin, achieving between 5–9 fold greater levels, at pre-maximum and maximum absorption times of 30 minutes and 1 hour, respectively. Orally administered pills containing biotin reached a level of only about 40,000 picograms/ml at the 1 hour level, an amount only ⅓ that of the microfluidized biotin when administered via the buccal mucosa. It is thus seen that administration of biotin via the buccal mucosa subsequent to formation of a microfluidized nanosuspension results in substantially higher absorption at a substantially higher rate than that which has heretofore been known in the prior art.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for administration of a biologically active agent to a subject via a buccal mucosal route comprising:

forming, via a microfluidization process, a stable nanosuspension comprising nanodroplets of at least one biologically active agent; and contacting said nanosuspension with the buccal mucosa of said subject;

wherein said biologically active agent is absorbed into the bloodstream of said subject.

2. The method of claim 1, wherein said subject is a human.

3. The method of claim 1, wherein said subject is an animal.

4. The method of claim 1, wherein said nanosuspension contains particles in a size range of about 87 nm to about 10 μm.

5. The method of claim 1, wherein said nanosuspension further includes a permeation enhancer.

6. The method of claim 1, wherein said biologically active agent is at least one nutritional product.

7. The method of claim 1, wherein said biologically active agent is at least one pharmaceutical product.

8.The method of claim 1, wherein said nanosuspension is in the form of a microfluidized spray, an aerosol, a tablet, a capsule, a pill, a liquid, a suppository, or a gel.

* * * * *